(12) United States Patent  (10) Patent No.: US 8,226,408 B2
Grant et al.  (45) Date of Patent: Jul. 24, 2012

(54) DENTAL ABUTMENT INCLUDING FILLET

(75) Inventors: Bethany F Grant, Scituate, MA (US); James G Hannoosh, Centerville, MA (US)

(73) Assignee: DENTSPLY International Inc., York, PA (US)

(*) Notice: Subject to any disclaimer, the term of this patent is extended or adjusted under 35 U.S.C. 154(b) by 211 days.

(21) Appl. No.: 12/450,573

(22) PCT Filed: Mar. 12, 2008

(86) PCT No.: PCT/EP2008/052953
§ 371 (c)(1),
(2), (4) Date: Dec. 2, 2009

(87) PCT Pub. No.: WO2008/110575
PCT Pub. Date: Sep. 18, 2008

(65) Prior Publication Data
US 2010/0119995 A1    May 13, 2010

Related U.S. Application Data

(60) Provisional application No. 60/918,078, filed on Mar. 14, 2007.

(51) Int. Cl.
*A61C 8/00* (2006.01)
(52) U.S. Cl. ........................................................ 433/173
(58) Field of Classification Search .................. 433/173, 433/174
See application file for complete search history.

(56) References Cited

U.S. PATENT DOCUMENTS

| | | | | |
|---|---|---|---|---|
| 5,328,371 A | * | 7/1994 | Hund et al. | 433/173 |
| 5,368,483 A | * | 11/1994 | Sutter et al. | 433/173 |
| 5,823,776 A | | 10/1998 | Duer et al. | |
| 5,873,721 A | * | 2/1999 | Willoughby | 433/173 |
| 6,315,563 B1 | * | 11/2001 | Sager | 433/173 |
| 6,447,295 B1 | * | 9/2002 | Kumar et al. | 433/172 |
| 6,503,083 B2 | * | 1/2003 | Chen | 433/174 |
| 6,726,480 B1 | | 4/2004 | Sutter | |
| 7,780,446 B2 | * | 8/2010 | Sanchez et al. | 433/173 |
| 2007/0254265 A1 | * | 11/2007 | Callan | 433/174 |

FOREIGN PATENT DOCUMENTS

| | | |
|---|---|---|
| CN | 1196670 | 10/1998 |
| DE | 195 34 979 | 9/1995 |
| EP | 1 419 746 A2 | 5/2004 |
| EP | 1 419 746 A3 | 4/2005 |

OTHER PUBLICATIONS

Office Action dated Aug. 5, 2010 for corresponding Australian Patent Application No. 2008225825.
Translation of Chinese Office Action dated Aug. 19, 2011 for corresponding Chinese Patent Application No. 200880008367.0.

* cited by examiner

*Primary Examiner* — Ralph Lewis
(74) *Attorney, Agent, or Firm* — David A. Zdurne; Douglas J. Hura; Leana Levin

(57) ABSTRACT

Exemplary embodiments relate to a dental abutment and methods of forming the same. The abutment (19) may include a head portion (27) located at an upper end of the abutment and constructed to support a prosthetic tooth replacement and soft tissue adjacent the head portion, an anti-rotation feature (25) located at a lower end of the abutment and constructed to mate with a dental implant, and a fillet (21) located at an interface between the head portion and the anti-rotation feature. The fillet may reduce a risk of fracture at the interface between the head portion and the anti-rotation feature. In some examples, the abutment may be formed at least partially of a ceramic material.

28 Claims, 8 Drawing Sheets

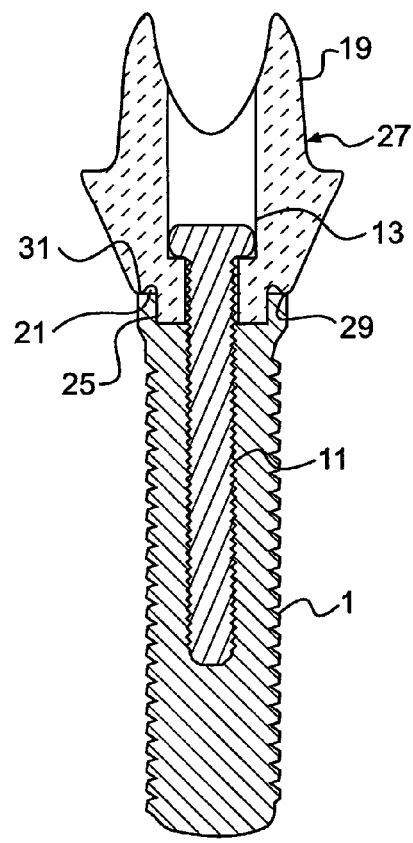
FIG. 6
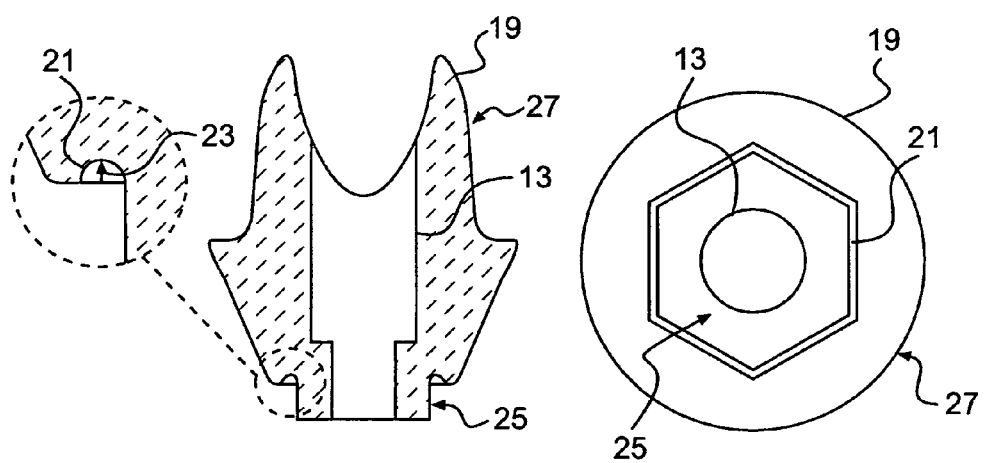
FIG. 7  FIG. 8

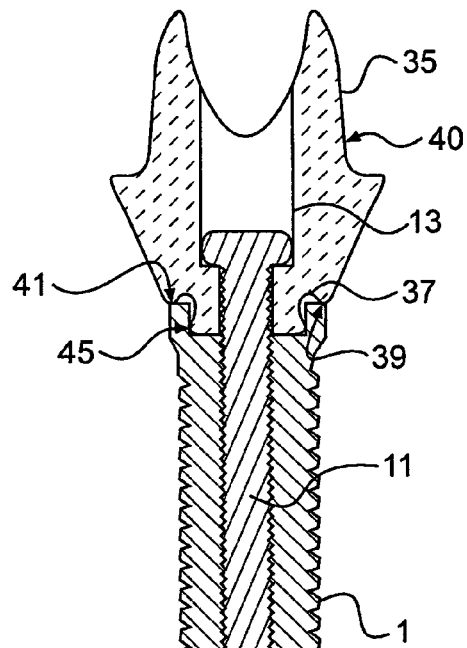
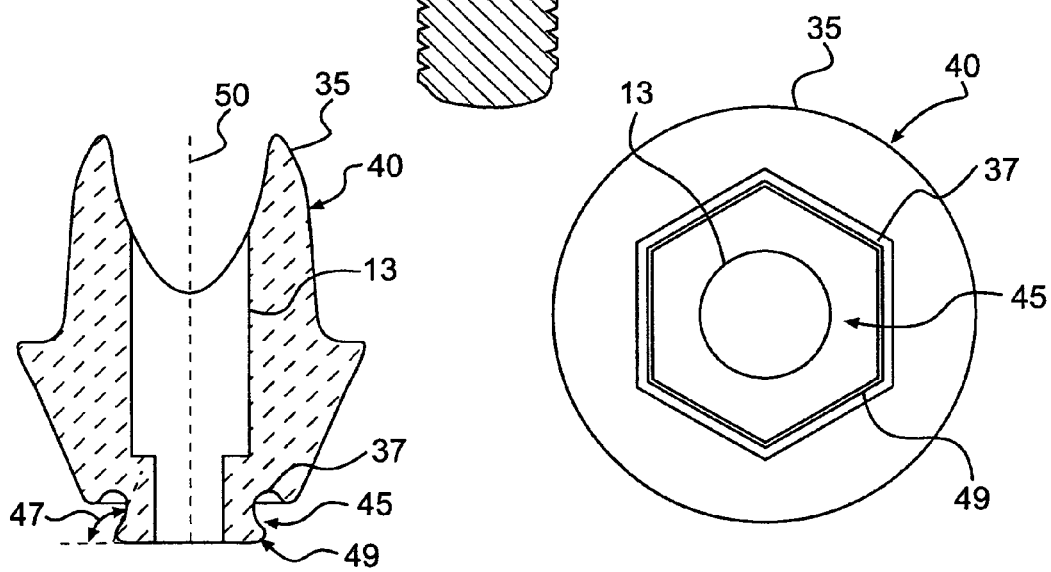
FIG. 9
FIG. 10
FIG. 11

DENTAL ABUTMENT INCLUDING FILLET

CROSS-REFERENCE TO RELATED APPLICATIONS

This application claims benefit under 35 U.S.C. §119(e) to U.S. Provisional Patent Application No. 60/918,078, filed on Mar. 14, 2007 in the United States Patent Office, and under 35 U.S.C. §119 to National Phase of PCT International Application No. PCT/EP2008/052953, filed on Mar. 12, 2008, the entire contents of each of which is hereby incorporated herein by reference.

FIELD OF THE INVENTION

This invention is directed to the field of dental abutments.

BACKGROUND OF THE INVENTION

Artificial tooth replacements are used in prosthetic dentistry to improve the appearance and/or functionality of a patient's teeth. A common artificial tooth replacement comprises a dental implant that is anchored within the bone, an abutment fastened to the implant with a screw, and a functional and aesthetic tooth replacement (a crown) positioned on the abutment. The abutment serves as the interface between the implant and the crown.

Traditionally, both the implant and the abutment are formed of metal (e.g., titanium or gold alloys), and the crown is often made entirely of ceramic. However, metal abutments have certain aesthetic drawbacks. First, where a patient's soft tissue (or gum tissue) are thinner, for example in the anterior, or front, region of the mouth, the gray color of the metal abutment can be seen through the soft tissue. In patients where soft tissue recedes below the level of the abutment, a portion of the metal abutment may be exposed above the soft tissue. Further, the metal abutment may sometimes be visible through an all-ceramic crown.

To improve the aesthetics of the tooth replacement, ceramics have been contemplated as alternative materials for the formation of abutments. Unlike metals, certain ceramics closely replicate the natural tooth in appearance—i.e., color and translucency. Ceramics, however, are much more brittle than titanium, such that it is challenging to design small shapes that resist breakage. Creation of a structurally sound ceramic dental abutment therefore presents many challenges.

SUMMARY OF THE INVENTION

In the following description, certain aspects and embodiments of the present invention will become evident. It should be understood that the invention, in its broadest sense, could be practiced without having one or more features of these aspects and embodiments. In other words, these aspects and embodiments are merely exemplary.

One aspect of the invention is directed to a dental abutment. The dental abutment may comprise a head portion located at an "upper" end of the abutment and constructed to support a prosthetic tooth replacement and soft tissue adjacent the head portion, an anti-rotation feature located at a "lower" end of the abutment and constructed to mate with a dental implant, and a fillet located at an interface between the head portion and the anti-rotation feature. The fillet may have a closed perimeter and may form a concavity at least partly in the head portion.

Another aspect of the invention is directed to a dental abutment comprising a head portion located at an upper end of the abutment and constructed to support a prosthetic tooth replacement and soft tissue adjacent the head portion, an anti-rotation feature located at a lower end of the abutment and constructed to mate with a dental implant, and a fillet located at an interface between the head portion and the anti-rotation feature (e.g., to reduce stress at the interface). The fillet may have a closed perimeter and may form a concavity at least partly in one of the anti-rotation feature and the head portion. A radial dimension of the fillet along a vertical cross-section of the fillet may be at least 0.1 mm.

A further aspect of the invention is directed to a dental assembly, comprising an implant and an abutment formed at least partially of a ceramic material. The implant may include an anchor portion located at a first end of the implant and adapted to be anchored within a jawbone, a mating feature located at a second end of the implant, and a rim surrounding the mating feature. The abutment may include a head portion located at an end of the abutment and adapted to support a prosthetic tooth replacement and soft tissue adjacent the head portion, a second portion comprising a seating surface, an anti-rotation feature located distally from the head portion of the abutment and adapted to mate with a corresponding feature of the implant in a manner that inhibits rotation of the abutment with respect to the implant, and a fillet located at an interface (i.e., transition) between the head portion and the anti-rotation feature, wherein the fillet may have a radial dimension of at least 0.1 mm along a vertical cross-section of the fillet. Mating the anti-rotation feature of the abutment to the implant may cause the rim of the implant to contact the seating surface of the abutment along a substantially closed region thereof.

Another aspect of the invention is directed to at least one computer readable medium encoded with instructions that, when executed on a computer system, perform a method comprising guiding a machine tool to fabricate a dental abutment. The abutment may comprise a head portion located at an upper end of the abutment and constructed to support a prosthetic tooth replacement and soft tissue adjacent the head portion, an anti-rotation feature located at a lower end of the abutment and constructed to mate with a dental implant, and a fillet having a closed perimeter. The fillet may be located at an interface (i.e., transition) between the head portion and the anti-rotation feature and may form a concavity at least partly in the head portion.

A further aspect of the invention is directed to a method comprising fabricating a dental abutment. The abutment may comprise a head portion located at an upper end of the abutment, such head portion being constructed and arranged to support a prosthetic tooth replacement and soft tissue adjacent the head portion, an anti-rotation feature located at a lower end of the abutment and constructed to mate with a dental implant, and a fillet having a closed perimeter. The fillet may be located at an interface (i.e., transition) between the head portion and the anti-rotation feature and may form a concavity at least partly in the head portion.

Another aspect of the invention is directed to a dental abutment, comprising a head portion located at an upper end of the abutment and constructed to support a prosthetic tooth replacement and soft tissue adjacent the head portion, an anti-rotation feature located at a lower end of the abutment and constructed to mate with a dental implant, and a fillet located at an interface between the head portion and the anti-rotation feature, wherein the fillet may have a closed perimeter and may form a concavity in the anti-rotation feature. A diameter of the anti-rotation feature at a location within the concavity may be smaller than a diameter of the anti-rotation feature at a location below the concavity.

A further aspect of the invention is directed to a method of fabricating a dental abutment comprising a fillet. The method may comprise selecting a radius for a fillet based on a critical flaw size of a material, and fabricating an abutment from the material, the abutment comprising a head portion located at an upper end of the abutment and constructed to support a prosthetic tooth replacement and soft tissue adjacent the head portion, an anti-rotation feature located at a lower end of the abutment and constructed to mate with a dental implant, and a fillet having the selected radius, wherein the fillet may be located at an interface between the head portion and the anti-rotation feature.

Aside from the structural and procedural arrangements set forth above, the invention could include a number of other arrangements such as those explained hereinafter. It is to be understood that both the foregoing description and the following description are exemplary only.

BRIEF DESCRIPTION OF THE DRAWINGS

The accompanying drawings are incorporated in and constitute a part of this specification. The drawings illustrate exemplary embodiments and, together with the description, serve to explain some principles of the invention. In the drawings.

FIG. 6 illustrates a longitudinal cross-sectional view of a first embodiment of an abutment in combination with an implant;

FIG. 7 illustrates an enlarged cross-sectional view of the abutment of FIG. 6;

FIG. 8 illustrates a bottom view of the abutment of FIG. 6;

FIG. 9 illustrates a longitudinal cross-sectional view of another embodiment of an abutment in combination with an implant;

FIG. 10 illustrates an enlarged cross-sectional view of the abutment of FIG. 9;

FIG. 11 illustrates a bottom view of the abutment of FIG. 9;

DETAILED DESCRIPTION OF THE EXEMPLARY EMBODIMENTS

Figure 1:
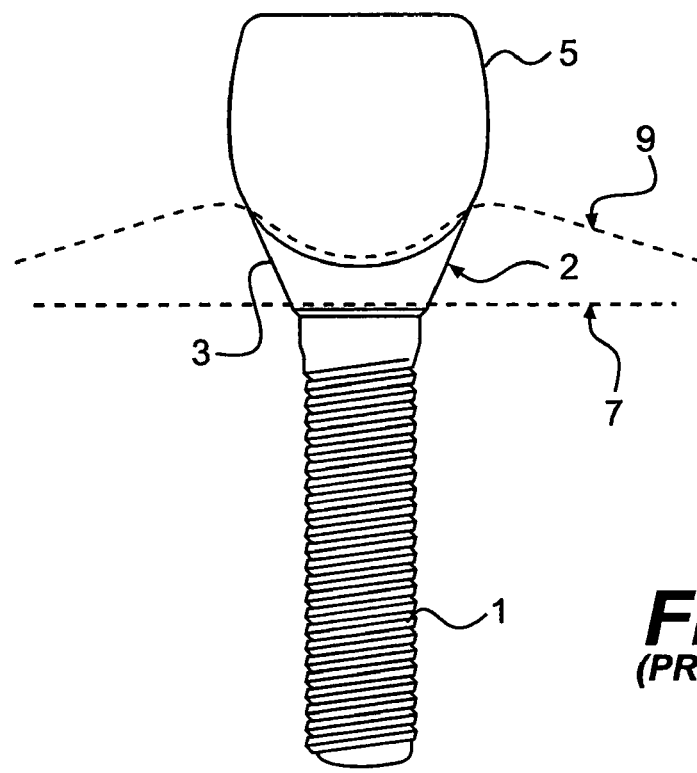
FIG. 1 illustrates a side view of a conventional artificial tooth replacement.
Figure 2:
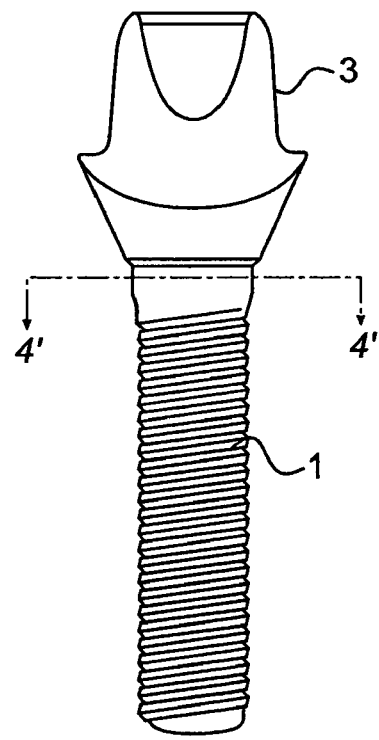
FIG. 2 illustrates a side view of the implant and abutment of FIG. 1.

FIGS. 1 and 2 illustrate a conventional artificial tooth replacement comprising a dental implant 1, an abutment 3, and a crown 5. In use, the implant 1 is anchored within a jawbone, the profile of which is shown by line 7. The abutment 3 is fixedly attached to the top of the implant 1, as shown in FIG. 2, and serves as an interface between the implant 1 and the crown 5. The crown 5 is positioned over the abutment 3 and is fixedly attached thereto. A tapered portion 2 of the abutment 3 may be positioned below the gum line 9 (as shown in FIG. 1) or at least only partially above the gum line 9. Thus, if the abutment 3 is formed of titanium, the grayish color of the abutment 3 may be visible above the gum line 9 or through the thin soft tissue of the gum just below the gum line 9. The titanium of the abutment therefore may give the artificial tooth replacement an unnatural and generally undesirable appearance.

Figure 3:
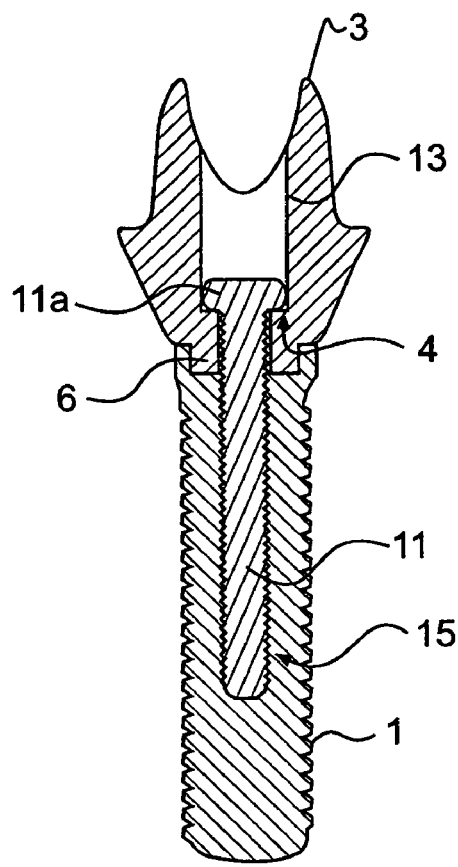
FIG. 3 illustrates a longitudinal cross-sectional view of the implant and abutment of FIG. 2.
Figure 4:
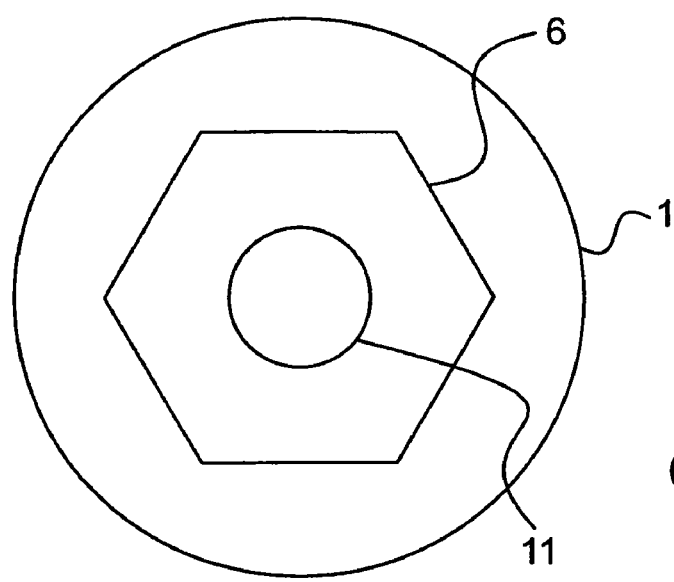
FIG. 4 illustrates a cross-sectional view of the implant and abutment of FIG. 2 along line 4'-4' of FIG. 2.

FIG. 3 illustrates a vertical cross-sectional view of a typical prior art implant and abutment combination of FIG. 2 through a central longitudinal axis of the abutment. As shown, a screw 11 is used to fixedly attach the abutment 3 to the implant 1. The screw 11 is introduced through a central bore 13 in the abutment 3 and is screwed into a threaded opening 15 of the implant 1. A head 11a of the screw 11 rests on a seating surface 4 of the abutment 3. The abutment also includes an anti-rotation feature 6. FIG. 4, which shows a cross-sectional view of the implant and abutment combination of FIG. 2 along line 4'-4' thereof, illustrates the anti-rotation feature 6.

FIG. 4 shows that the anti-rotation feature 6 has a hexagonal cross-section. This shape prevents rotation of the abutment 3 with respect to the implant 1. The anti-rotation feature 6 is described as an "internal connection," because the feature 6 is in the form of a protrusion that mates with the implant 1 internal to the implant 1. In other implant/abutment combinations, the anti-rotation feature of the abutment comprises a socket rather than a protrusion, and mates with the implant external to the implant. In this case, the anti-rotation feature is described as an "external connection."

As explained above, ceramic abutments sometimes provide an improved aesthetic relative to titanium abutments, because the color of the ceramic may be selected to be close to or identical to a natural tooth color. However, the properties of ceramic materials sometimes necessitate a design approach different than that of an all-metal system. Ceramic materials may be brittle, and susceptible to catastrophic failure if local stresses in the material reach values near the strength of the material. At least some metals, on the other hand, may yield locally when stresses reach values near the strength of the material, providing a stress relief mechanism for the system.

Figure 5:
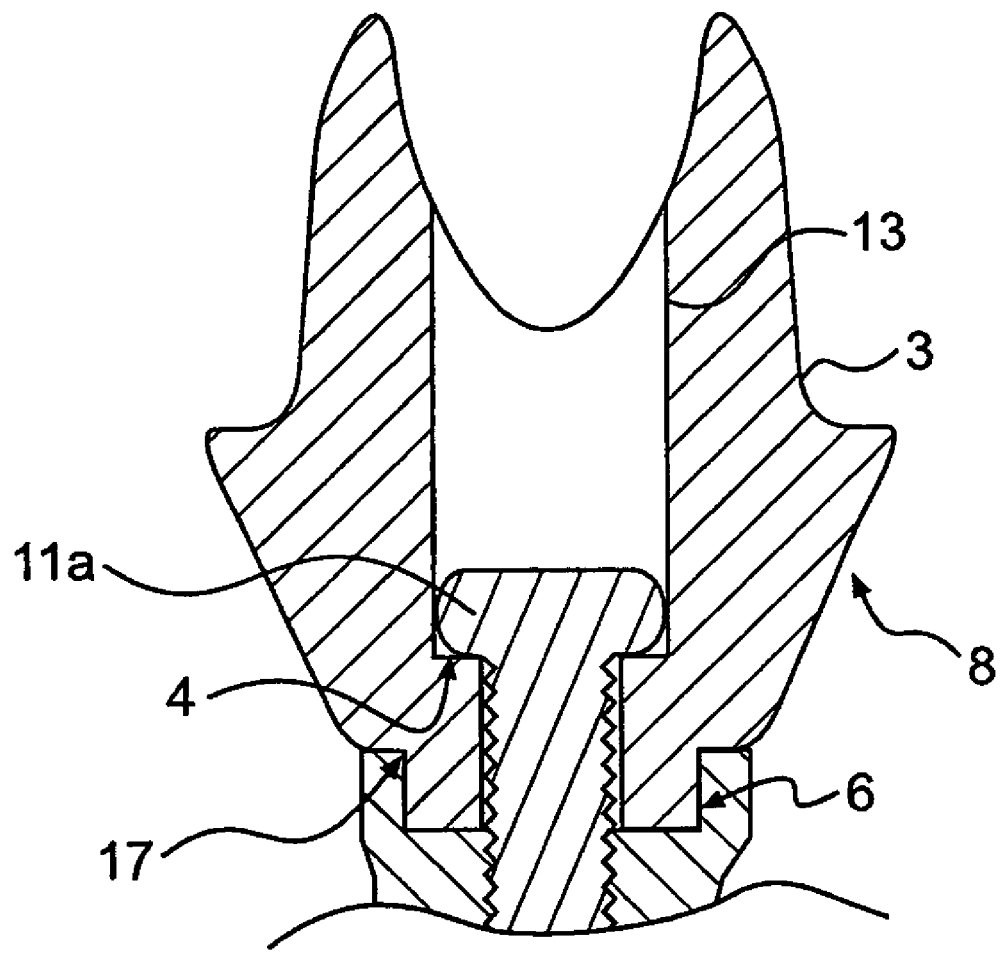
FIG. 5 illustrates an enlarged cross-sectional view of the abutment of FIG. 2.

One example of this phenomenon is exemplified by the geometry shown in FIG. 5, which illustrates an enlarged cross-sectional view of a portion of the implant 1 and abutment 3 combination shown in FIG. 3. As shown, the interface between anti-rotation feature 6 of the abutment 3 and the head 8 of the abutment 3 is nearly a right angle 17 (i.e., a corner of a very small radius). Because local stresses are highest near sharp corners, the region of the right angle 17 is a high stress area. A metal abutment subjected to loads causing stresses near the strength of the material in this region could result in localized yielding, in the form of prying open the angle between abutment head 8 and anti-rotation feature 6. However, if the abutment 3 were formed of ceramic, subjecting the abutment 3 to loads causing stresses (e.g., tensile stresses) near the strength of the ceramic material in the same region at angle 17 could have a high probability of catastrophic failure, or fracture.

Abutment with Reduced Stress Concentrations

FIGS. 6-8 show a first embodiment of an example of an abutment according to the invention, which may be formed of ceramic material. FIG. 6 illustrates a vertical cross-sectional view of an implant and abutment combination through a central longitudinal axis of the abutment, and FIG. 7 illustrates an enlarged cross-sectional view of the exemplary abutment alone. The implant and abutment combination of FIG. 6 is similar to that shown in FIG. 3, but comprises an abutment 19 that is configured to reduce the risk of fracture at the implant/abutment interface even when the abutment 19 is formed of ceramic material or another material that may be susceptible to failure. In particular, the abutment 19 incorporates a fillet 21 at the transition region (i.e., interface) between the anti-rotation feature 25 and the head 27 of the abutment 19. The fillet 21 eliminates the sharp corner that would be present at a right-angle (or nearly right angle) interface between the anti-rotation feature 25 of the abutment 19 and the head 27 of the abutment 19. The fillet 21 may have any form of concave curvature, including circular and/or non-circular (e.g., elliptical or any other shape having a generally curved portion). For example, it may have a generally circular profile with the radius 23, as best shown in FIG. 7. In the embodiment of FIGS. 6-8, the fillet 21 forms a concavity in the head 27 of the abutment 19. Although the concavity shown in the example of FIGS. 6-8 does not extend to the anti-rotation feature 25, in alternative configurations, the fillet may be configured to form a concavity in both the head 27 and the anti-rotation feature 25 or in only the anti-rotation feature 25. Consequently, unless otherwise qualified, expressions such as "at the transition region" and "at the interface" (and similar expressions such as "in the transition region," "in the interface," "in/at a transition region," and "in/at an interface"), with respect to the fillet, contemplates this range of fillet sharing between the anti-rotation feature and the abutment head portion.

FIG. 8 illustrates a bottom view of the abutment 19. As discussed above, the fillet 21 is located at—and comprises at least part of—the transition region between the anti-rotation feature 25 and the head 27 of the abutment 19. In this example, both the anti-rotation feature 25 and the fillet 21 are hexagonal in the transverse cross-section view of FIG. 8.

According to one exemplary implementation, a vertical cross-section of the fillet 21 has a radius 23 of at least 0.05 mm. For example, the radius 23 may be at least approximately 0.1 mm or at least approximately 0.2 mm. The radius 23 of the fillet 21, or any of the other fillets described herein, may be selected based on a critical flaw size of the material from which the abutment 19 is constructed. Thus, the fillet 21 may be dimensioned based on the size of a defect that will cause failure in that material at a particular stress level. The vertical cross section may have an arcuate shape (e.g., circular or elliptical), although other configurations are possible. The radius 23 of the fillet 21 may be uniform along the perimeter of the fillet, as shown in FIG. 8, or it may vary. The larger the radius 23 of the fillet 21, the less concentrated the stress at the fillet will be. Accordingly, it may be desirable to maximize the radius 23 of the fillet 21 within certain parameters.

In particular, it may be desirable to maximize the radius 23 of the fillet 21 while maintaining sufficient contact between a seating surface 29 of the abutment 19 and a rim 31 of the implant 1. If the radial contact between the seating surface 29 and the rim 31 becomes too small at any location, the abutment 19 may not properly seal the opening of the implant 1. This may create an undesirable configuration of the system, potentially allowing bacteria to enter the implant-abutment connection. According to one exemplary implementation, the abutment 19 is constructed to have a minimum of 0.1 mm to 0.2 mm of contact between the seating surface 29 and the rim 31, when measured radially from the center of the implant 1, to ensure a sufficient seal between the abutment 19 and the implant 1. In the embodiment of FIGS. 6-8, increasing the size of the radius 23 generally decreases the radial contact between the seating surface 29 of the abutment 19 and the rim 31 of the implant 1. To avoid decreasing the radial contact between the seating surface 29 and the rim 31 to undesirable levels, increasing the radius 23 of the fillet 21 can be balanced with maintaining sufficient contact between the seating surface 29 of the abutment 19 and the rim 31 of the implant 1.

It may be desirable to increase the radius 23 of the fillet 21 without sacrificing the amount of radial contact between the seating surface 29 of the abutment 19 and the rim 31 of the implant 1. One way to do so would be to increase the width of the rim 31 of the implant 1 and the width of the seating surface 29 of the abutment 19. However, because the dimensions of the implant 1 may be fixed, for example if the abutment 19 is designed to be compatible with implants 1 of known dimensions, a solution that relies only on the construction of the abutment 19 may be preferable.

To increase the radius 23 of the fillet 21 without sacrificing the amount of radial contact between the seating surface 29 of the abutment 19 and the rim 31 of the implant 1, and without modifying the implant 1, the contour of the anti-rotation feature 25 may be modified. FIGS. 9-11 illustrate one exemplary implementation of an abutment 35 in which the contour of the anti-rotation feature 45 is modified for this purpose. The abutment 35 shown in FIGS. 9-11 may be formed of ceramic materials and may have a fillet 37 at the interface between the head 40 and the anti-rotation feature 45 of the abutment 35. However, relative to the embodiment of FIGS. 6-8, the radius of the fillet 37 is increased and the contact between the seating surface 39 of the abutment 35 and the rim 41 of the implant 1 is maintained.

As shown in FIGS. 9 and 10, the outer contour of anti-rotation feature 45 angles inwardly toward the central longitudinal axis 50 of the implant as the height of the anti-rotation feature 45 increases. The angle 47 between the plane occupied by the bottom of the abutment 35 and an outer contour of the anti-rotation feature 45 is greater than 90° but less than 180°. For example, the angle 47 may be between about 91° and about 130°. As shown in FIGS. 9-11, the lower portion of the anti-rotation feature 45 may include a chamfer or a radius 49 to facilitate insertion of the anti-rotation feature 45 into the implant 1.

Figure 12:
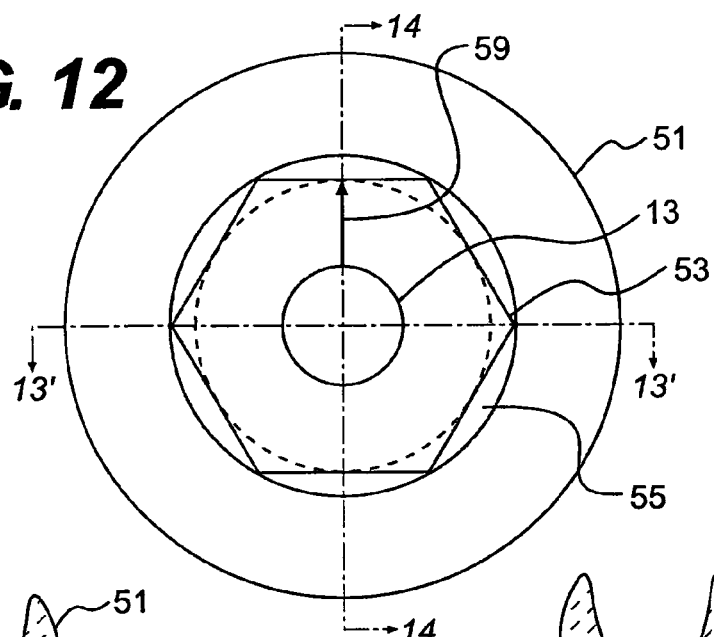
FIG. 12 illustrates a bottom view of a further embodiment of an abutment.
Figure 13:
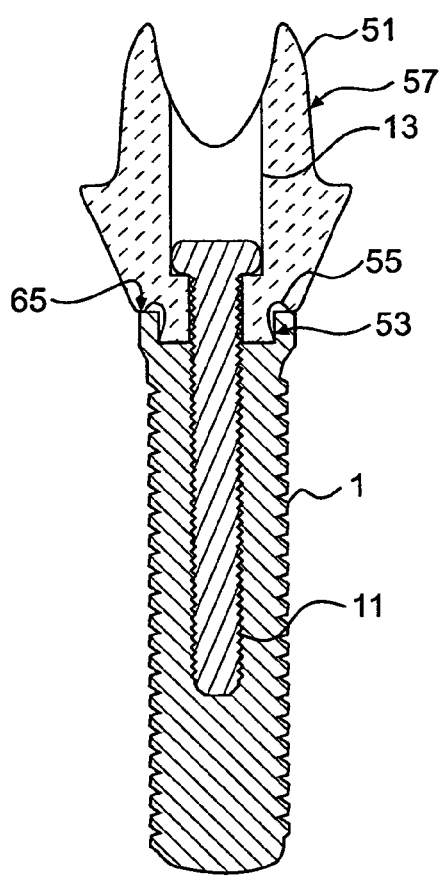
FIG. 13 illustrates a cross-sectional view of the abutment of FIG. 12 along line 13'-13' of FIG. 12, in combination with an implant.
Figure 14:
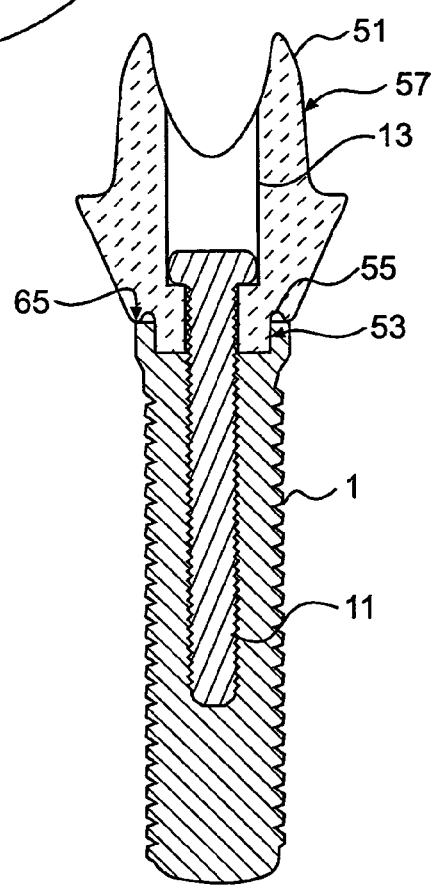
FIG. 14 illustrates a cross-sectional view of the abutment of FIG. 12 along line 14-14 of FIG. 12, in combination with an implant.

While the inward angling of the outer contour of the anti-rotation feature 45 may advantageously allow the radius of the fillet 37 to be increased, in certain circumstances such angling could reduce the radial thickness of the anti-rotation feature 45 of the abutment 35 to undesirable levels. One way to avoid this result is to angle the outer contour of the anti-rotation feature 45 only in those locations where it would not cause the minimum thickness of the anti-rotation feature 45 to be reduced. FIGS. 12-14 show an exemplary implementation of an abutment 51 including an anti-rotation feature 53 that is selectively angled so as not to reduce the minimum thickness of the anti-rotation feature 53. FIG. 12 illustrates a bottom view of the abutment 51, which may be formed of ceramic material. As shown in FIG. 12, the anti-rotation feature 53 is hexagonal and the fillet 55 at the interface of the abutment head 57 and the anti-rotation feature 53 is circular. The portion of the contour of the fillet 55 that is obscured by the anti-rotation feature 53 is shown in phantom.

As shown in FIG. 12, the anti-rotation feature 53 has a larger radial dimension at the points of the hexagon relative to the sides of the hexagon. Thus, material can be removed from the anti-rotation feature 53 in the vicinity of the points, without reducing the minimum thickness 59 of the anti-rotation feature 53, as measured from the boundary of the central bore 13 to the outer portion of the anti-rotation feature 53.

FIGS. 13 and 14 illustrate different views of the abutment 51 in combination with an implant 1 and a screw 11. In particular, FIG. 13 illustrates a cross-sectional view of the abutment 51 along line 13'-13' of FIG. 12 in combination with the implant 1. FIG. 1 illustrates a cross-sectional view of the abutment 51 along line 14-14 of FIG. 12 in combination with the implant 1. In the cross-section of FIG. 13, the anti-rotation feature 53 is inwardly angled. The minimum thickness of the anti-rotation feature 53 in this cross-section occurs at the upper portion of the anti-rotation feature 53, where the inward angle of the anti-rotation feature 53 interfaces with the fillet 55. In FIG. 14, the anti-rotation feature 53 is not angled. The minimum thickness of the anti-rotation feature 53 in this cross-section is uniform, and is equal to or less than the minimum thickness 59 of the anti-rotation feature 53 in the cross-section shown in FIG. 12. The rim 65 of the implant 1 is wider in the cross-sectional view of FIG. 14 than in the cross-sectional view of FIG. 13, because the inner contour of the rim 65 has a hexagonal shape to match the shape of the anti-rotation feature 53.

Figure 15:
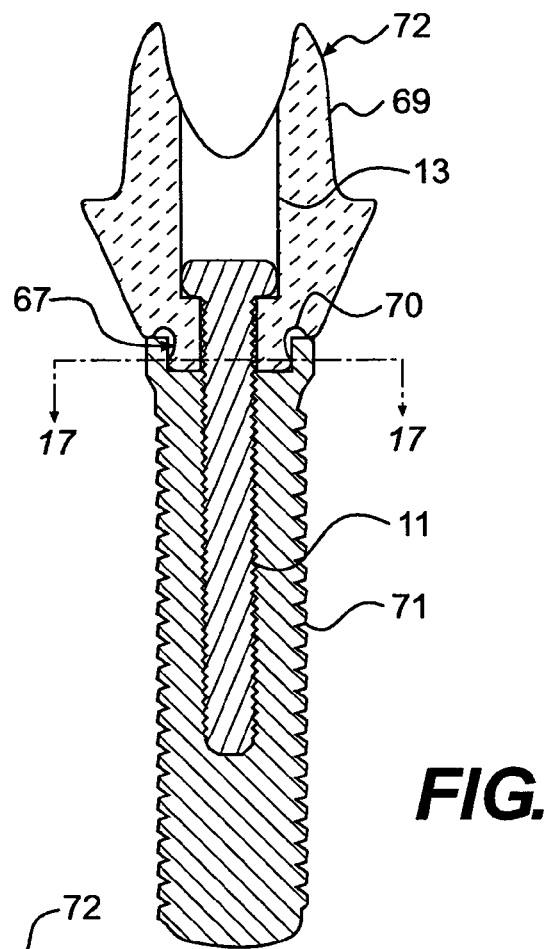
FIG. 15 illustrates a longitudinal cross-sectional view of another embodiment of an abutment in combination with an implant.
Figure 16:
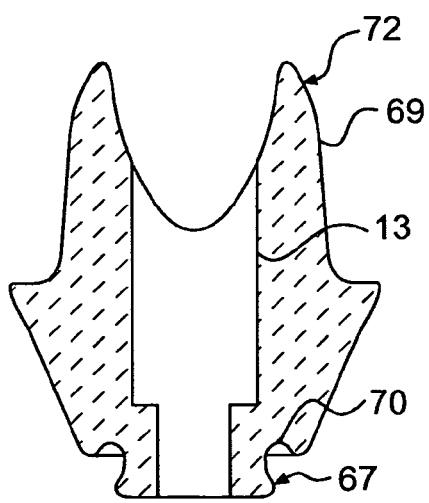
FIG. 16 illustrates an enlarged cross-sectional view of the abutment of FIG. 15.
Figure 17:
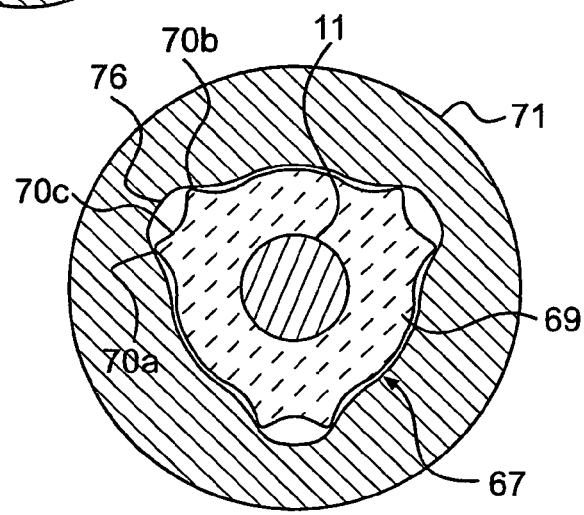
FIG. 17 illustrates a cross sectional view of the abutment and implant combination of FIG. 15 along line 17-17 of FIG. 15.

While some of the anti-rotation features described herein have a hexagonal shape, it should be appreciated that the invention is not limited in this respect. Many other non-circular shapes (e.g., octagonal, square, oval, lobed, and rectangular) may alternatively be used. For example, FIGS. 15-17 illustrate an embodiment wherein the anti-rotation feature 67 of an abutment 69 has a lobed shape. As in previous embodiments, the abutment 69 comprises a fillet 70 at the interface of the head portion 72 and the anti-rotation feature 67. FIG. 15 illustrates a cross-sectional view of the abutment 69 in combination with an implant 71, and FIG. 16 illustrates an enlarged cross-sectional view of the abutment 69 alone. As shown in FIGS. 15-16, a portion of the outer contour of the anti-rotation feature 67 of the abutment 69 is angled, as in some of the above embodiments. However, the angling begins part-way (e.g., mid-way) up the anti-rotation feature 67. FIG. 17 illustrates a cross-sectional view of the implant 71 and the abutment 69 of FIG. 15 through line 17-17 thereof.

In any of the embodiments described herein, the abutment may be formed of a ceramic material. Exemplary ceramic materials include at least zirconium oxide or "zirconia" ($ZrO_2$) (e.g., yttria-stabilized tetragonal zirconia polycrystals), aluminum oxide or "alumina" ($Al_2O_3$), and silicon dioxide or "silica" ($SiO_2$). It should be appreciated that the abutment may be formed either partially or fully of a ceramic material. For example, the abutment may be formed of a ceramic composite, such as a ceramic and polymer composite, a ceramic and metal matrix composite, or a ceramic matrix composite. All such possibilities are intended to be encompassed within the terms "ceramic material." Further, the abutment may be formed of ceramic and non-ceramic physical sections.

The implant described herein has been presented as formed of titanium. However, in any of the embodiments described herein, the implant may alternatively be formed, in whole or in part, of any of the ceramic materials described above.

The abutments of the embodiments described herein may be formed using a high-performance, multi-axis (e.g., three-, four-, or five-axis) machine tool. Examples of suitable machine tools include model XR 610 manufactured by Hardinge Inc. of Elmira, N.Y.; model VF-1 manufactured by Haas Automation, Inc. of Oxnard, Calif.; and model SMM-2000 manufactured by Mazak Corporation of Florence, Ky. The machine tool may be controlled by a computer, for example in response to instructions read from a computer readable medium and executed on the computer. The executed instructions may perform any of the methods described herein and form any of the exemplary abutment configurations described herein. For example, one or more computer readable media may be encoded with instructions that, when executed on a computer system, guide a machine tool to fabricate a dental abutment (e.g., from a ceramic material), the abutment comprising a fillet located at an interface between a head portion and an anti-rotation feature of the abutment.

Figure 18:
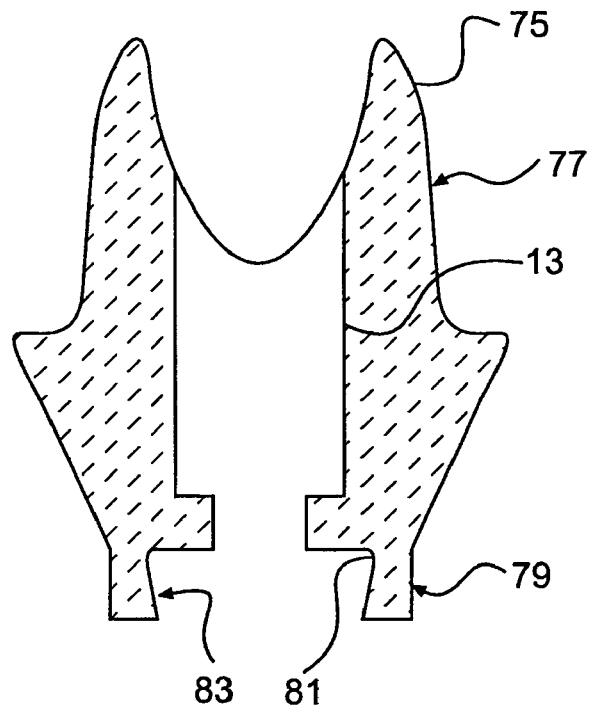
FIG. 18 illustrates a cross-sectional view of a further embodiment of an abutment.

As described herein, in some implant/abutment combinations, the anti-rotation feature of the abutment may form an external connection rather than an internal connection. The principles described herein for providing a fillet at the interface between the head of an abutment and the anti-rotation feature of the abutment to reduce the likelihood of fracture may also be applied to an abutment having an external connection. For example, FIG. 18 shows a cross-sectional view of an abutment 75 having a head portion 77 and an external anti-rotation feature 79. A fillet 81 is provided at the interface of the head portion 77 and the anti-rotation feature 79, which eliminates the sharp corner that would otherwise be present. In this example, the concavity formed by the fillet 81 is located entirely in the anti-rotation feature 79 and not in the head portion 77, however other arrangements are possible. For example, the concavity may be located partially or entirely in the head portion 77 as described in connection with other embodiments. Further, portions of the inner wall 83 of the anti-rotation feature 79 may be inwardly angled, as shown, for the reasons described herein. The fillet 81 and the angle of the wall 83 may be configured in any of the manners described herein in connection with other embodiments. For example, the fillet 81 may have a vertical cross-section having a radius of at least 0.05 mm, 0.1 mm or 0.2 mm, and may have an arcuate shape (e.g., circular or elliptical). Further, the other embodiments described herein may have features shown in FIG. 18, e.g., an external connection or a concavity located entirely in the anti-rotation feature 79.

Figure 19:
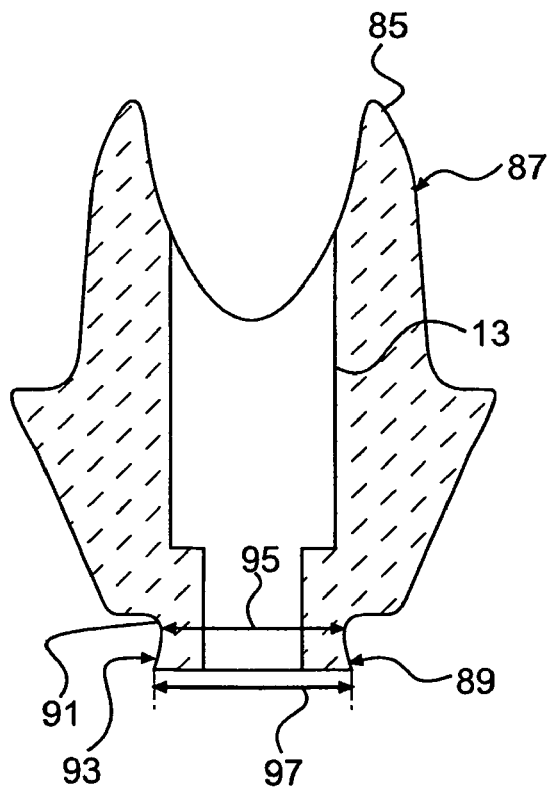
FIG. 19 illustrates cross-sectional view of another embodiment of an abutment.

For example, FIG. 19 illustrates a cross-sectional view of an abutment having a concavity that is located entirely within the anti-rotation feature of the abutment 85. In particular, the abutment 85 comprises a head portion 87 and an internal anti-rotation feature 89, similar to other internal connections described herein. A fillet 91 is provided at the interface of the head portion 87 and the anti-rotation feature 89. The concavity formed by the fillet 91 is located entirely in the anti-rotation feature 89 and not in the head portion 87. The fillet 91 is formed such that a diameter 95 of the anti-rotation feature 89 at a location within the concavity is smaller than a diameter 97 of the anti-rotation feature 89 at a location below the concavity. Portions of the wall 93 of the anti-rotation feature 89 may be inwardly angled, as shown, for the reasons described herein. The fillet 91 and the angle of the wall 93 may be configured in any of the manners described herein in connection with other embodiments. For example, the fillet may have a vertical cross-section having a radius of at least 0.05 mm, 0.1 mm or 0.2 mm, and may have an arcuate shape (e.g., circular or elliptical).

Abutment with Line Contacts with Implant

It may be appreciated from the foregoing that contact between an anti-rotation feature of an abutment and a corresponding mating feature of an implant impedes rotation of the abutment with respect to the implant. The contact between the anti-rotation feature of the abutment and the mating feature of the implant may take many forms. For example, the contact may occur at one or more points, along one or more lines, or along one or more surfaces.

Surface contacts generally result from an interference fit. An interference fit involves inserting one member into another whose dimensions are slightly smaller than the part being inserted. In some cases, a surface contact may be undesirable for the anti-rotation feature of a ceramic abutment, because the ceramic anti-rotation feature may fracture due to high stresses caused by forcing it onto an implant. Thus, a clearance fit, which has the dimensions of the part being inserted being slightly smaller than the dimensions of the receiving feature, may be more suitable for the connection between an anti-rotation feature of a ceramic abutment and a mating feature of an implant. However, when designing an anti-rotation feature for a clearance fit, the precision of the fit depends on the accuracy of each component.

The demands on precision and accuracy for the fit of an abutment-implant assembly may be driven by the users' ability to rotate or move the abutment with respect to the implant. The size of the parts in question and the ability of machine tools limit the minimum clearance designed between the two parts. Implants are often constructed with anti-rotation features consisting of prisms. Different implants employ various cross-sections, including hexagons, octagons, or semi-circular lobes protruding from a central circle. Standard abutments designed to interface with these implants generally use shapes that are similar to that of the implant. In order to best control the clearance requirements between the abutment and implant, the abutment interface feature can be constructed to mate with the implant at points around the prism's cross-section, rather than mimicking the shape of the implant. This method enables better control of the relative fit of the parts, by requiring high precision in only limited regions.

Referring again to FIG. 17, which illustrates a cross-sectional view of the implant 71 and abutment 69 combination, the location of several line contacts are illustrated. For example, line contacts are formed along the lines that extends longitudinally along the abutment 69 at points 70*a* and 70*b*. Surface contacts could alternatively be used in place of any of the illustrated line contacts. For example, a surface contact along the semi-circle 76 of the implant 71 could be formed in place of the line contacts that traverse points 70*a* and 70*b*. However, it may be easier to control precisely the contact of the abutment 69 with the implant 71 when line contacts are used; therefore, line contacts may be preferable.

Although FIG. 17 shows a anti-rotation feature 67 in the form of points 70*a* and 70*b* that define a concave region 70*c* between them, a hexagonal anti-rotation feature also may be constructed advantageously to form line contacts with the implant. For example, if either the anti-rotation feature of the abutment or the corresponding mating feature of the implant is not perfectly hexagonal, such that the implant and the abutment do not have precisely matched shapes, line contacts can be formed at the regions of contact between the implant and the abutment. Applying similar principles, anti-rotation features having other shapes can also be constructed to form line contacts with an implant.

Although the abutments disclosed herein are described as being formed from a ceramic material, it should be appreciated that the abutments may be alternatively formed from non-ceramic materials (e.g., metals, composites, polymers, and other crystalline structures). Doing so may be particularly advantageous when such materials are brittle or susceptible to failure when used to form an abutment; however, the invention is not limited in this respect.

It should be appreciated that the principles described herein for reducing the risk of fracture at an interface are not limited to application in dental abutments and may be applied to non-abutment structures. For example, the design features described herein may be beneficially applied in the manufacture of screw heads, crowns, or implants. In particular, at interface regions or other areas of such non-abutment structures that are ordinarily implemented using a sharp angle, a fillet may be provided in the manner described herein. These non-abutment structures may be manufactured from the ceramic materials or non-ceramic materials described herein.

Having thus described at least one illustrative embodiment of the invention, various alterations, modifications and improvements will readily occur to those skilled in the art. Such alterations, modifications and improvements are intended to be within the scope of the invention. Accordingly, the foregoing description is by way of example only and is not intended as limiting.

The invention claimed is:

1. A dental abutment, comprising:
    a head portion located at an upper end of the abutment and constructed to support a prosthetic tooth replacement and soft tissue adjacent the head portion;
    an anti-rotation feature located at a lower end of the abutment and constructed to mate with a dental implant; and
    a fillet located at an interface between the head portion and the anti-rotation feature, the fillet having a closed perimeter and forming a concavity at least partly in one of the anti-rotation feature and the head portion;
    wherein the anti-rotation feature comprises one or more portions that are angled inwardly toward a central longitudinal axis of the abutment as the height of the anti-rotation feature increases.

2. The dental abutment of claim 1, wherein a radial dimension of the fillet along a vertical cross-section of the fillet is at least 0.1 mm.

3. The dental abutment of claim 1, wherein the abutment is formed at least partially of a ceramic material.

4. The dental abutment of claim 1, wherein the abutment is formed at least partially of material selected from the group consisting of zirconia, alumina and silica.

5. The dental abutment of claim 1, wherein each of the one or more inwardly angled portions has a minimum thickness where the inwardly angled portion abuts the fillet.

6. The dental abutment of claim 1, wherein the anti-rotation feature is an internal connection.

7. The dental abutment of claim 1, wherein the perimeter of the fillet is circular.

8. The dental abutment of claim 1, wherein the interface between the head portion and the anti-rotation feature of the abutment does not comprise any right angle.

9. The dental abutment of claim 1, wherein the anti-rotation feature has a non-circular shape.

10. The dental abutment of claim 1, wherein the concavity is entirely in the head portion.

11. A dental abutment, comprising:
    a head portion located at an upper end of the abutment and constructed to support a prosthetic tooth replacement and soft tissue adjacent the head portion;
    an anti-rotation feature located at a lower end of the abutment and constructed to mate with a dental implant; and a fillet located at an interface between the head portion and the anti-rotation feature, the fillet having a closed perimeter and forming a concavity at least partly in one of the anti-rotation feature and the head portion;

wherein a diameter of the anti-rotation feature at a location within the concavity is smaller than a diameter of the anti-rotation feature at a location below the concavity.

12. The dental abutment of claim 11, wherein a radial dimension of the fillet along a vertical cross-section of the fillet is at least 0.1 mm.

13. The dental abutment of claim 11, wherein the abutment is formed at least partially of a ceramic material.

14. The dental abutment of claim 11, wherein each of the one or more inwardly angled portions has a minimum thickness where the inwardly angled portion abuts the fillet.

15. The dental abutment of claim 11, wherein the anti-rotation feature is an internal connection.

16. The dental abutment of claim 11, wherein the perimeter of the fillet is circular.

17. The dental abutment of claim 11, wherein the interface between the head portion and the anti-rotation feature of the abutment does not comprise any right angle.

18. The dental abutment of claim 11, wherein the anti-rotation feature has a non-circular shape.

19. The dental abutment of claim 11, wherein the concavity is entirely in the head portion.

20. A method of fabricating a dental abutment comprising the steps of:

machining a dental abutment having:

a head portion located at an upper end of the abutment, the head portion being constructed and arranged to support a prosthetic tooth replacement and soft tissue adjacent the head portion, an anti-rotation feature located at a lower end of the abutment and constructed to mate with a dental implant, and a fillet having a closed perimeter, the fillet located at an interface between the head portion and the anti-rotation feature and forming a concavity at least partly in the head portion;

wherein the anti-rotation feature comprises one or more portions that are angled inwardly toward a central longitudinal axis of the abutment as the height of the anti-rotation feature increases.

21. The method of claim 20, wherein the abutment is formed at least partially of a ceramic material.

22. The method of claim 20, wherein the fillet comprises a radial dimension along a vertical cross-section of the fillet and wherein the radial dimension is at least 0.1 mm.

23. The method of claim 20, wherein the abutment is formed at least partially of material selected from the group consisting of zirconia, alumina and silica.

24. The method of claim 20, wherein each of the one or more inwardly angled portions has a minimum thickness where the inwardly angled portion abuts the fillet.

25. The method of claim 20, wherein the anti-rotation feature is an internal connection.

26. The method of claim 20, wherein the perimeter of the fillet is circular.

27. The method of claim 20, wherein the interface between the head portion and the anti-rotation feature of the abutment does not comprise any right angle.

28. The method of claim 20, wherein the anti-rotation feature has a non-circular shape.

* * * * *